(12) United States Patent
Mimoun

(10) Patent No.: US 7,528,268 B2
(45) Date of Patent: May 5, 2009

(54) PROCESS FOR THE PREPARATION OF LACTONES OR EPOXIDES

(75) Inventor: Hubert Mimoun, Challex (FR)

(73) Assignee: Firmenich SA, Geneva (CH)

( * ) Notice: Subject to any disclaimer, the term of this patent is extended or adjusted under 35 U.S.C. 154(b) by 570 days.

(21) Appl. No.: 11/210,501

(22) Filed: Aug. 23, 2005

(65) Prior Publication Data

US 2005/0283008 A1 Dec. 22, 2005

Related U.S. Application Data

(63) Continuation of application No. PCT/IB2004/000595, filed on Mar. 1, 2004.

(30) Foreign Application Priority Data

Mar. 4, 2003 (EP) ................................. 03004759

(51) Int. Cl.
*C07D 3012/12* (2006.01)

(52) U.S. Cl. ...................... 549/531; 549/272; 549/273; 502/340; 502/344

(58) Field of Classification Search ................ 549/272, 549/273, 295, 531, 522; 502/340, 344
See application file for complete search history.

(56) References Cited

U.S. PATENT DOCUMENTS

| 4,150,241 A | 4/1979 | Prescher et al. ............. 562/585 |
| 4,213,906 A | 7/1980 | Mares et al. ................ 260/343 |
| 4,590,286 A * | 5/1986 | Bull ........................... 549/526 |
| 5,026,881 A * | 6/1991 | Gruber ....................... 549/531 |
| 5,665,891 A | 9/1997 | Brown et al. ................ 549/272 |

FOREIGN PATENT DOCUMENTS

| DE | 100 41 510 A1 | 4/2001 |
| EP | 1 078 922 A1 | 2/2001 |

OTHER PUBLICATIONS

Paul T. Anastas et al., "Catalysis As A Foundational Pillar Of Green Chemistry", Applied Catalysis A: General 221, pp. 3-13 (2001).

* cited by examiner

*Primary Examiner*—Bernard Dentz
*Assistant Examiner*—David E Gallis
(74) *Attorney, Agent, or Firm*—Winston & Strawn LLP

(57) ABSTRACT

The present invention relates to a process for the oxidation, in an inert solvent, of a non-aromatic or non-enonic ethylenic bond or of a non-conjugated cyclic ketones into the corresponding epoxides, respectively lactone, using $H_2O_2$ as oxidant, a content in water of the reaction medium below 15% w/w and, as sole catalyst, an alkaline or alkaline earth salt or complex.

16 Claims, No Drawings

PROCESS FOR THE PREPARATION OF LACTONES OR EPOXIDES

CROSS-REFERENCE TO RELATED APPLICATIONS

This application is a continuation of International application PCT/IB2004/000595 filed Mar. 1, 2004, the entire content of which is expressly incorporated herein by reference thereto.

TECHNICAL FIELD

The present invention relates to the field of organic synthesis. More particularly it provides a new process for the oxidation of a substrate containing a non-aromatic or non-enonic ethylenic bond or a non-conjugated cyclic ketone into the corresponding epoxide, respectively lactone, using $H_2O_2$ as oxidant.

BACKGROUND

The so-called Baeyer-Villiger oxidation or the epoxidation of olefins is a type of reaction well documented in the prior art. Amongst the different primary oxidants which may be used in these two type of reactions, the most attractive is $H_2O_2$. However, when $H_2O_2$ is used, it is necessary to add a catalyst capable of generating an active species.

The catalysts used in the processes reported in the prior art, and which use $H_2O_2$ as oxidant, are either a heavy-metal derivative, e.g. a salt, complex, silicate or oxide, or a percarboxylic acid derivative, or a precursor of said acid derivative such as a mixture of a nitrile, carboxylic acid or carboxylic anhydride or chloride with $H_2O_2$. By the expression "heavy-metal" we mean here metals other than the alkaline or alkaline earth metals.

As example of such known processes, one may cite the one described by S. Ueno et al. in *Chem. Commun.*, 1998, 295, wherein olefins are epoxidized in the presence of $H_2O_2$, hydrotalcite $(Mg_{10}Al_{12}(OH)_{24}CO_3)$ and benzonitrile. Or alternatively, one can cite A. M. d'A. Rocha Gonsalves et al. in *J. Chem. Research.*, 1991, 208, wherein olefins are epoxidized by using a buffered solution of a percarboxylic derivative. More recently, M. C. A. van Vliet et al. in *Green Chemistry*, 2001, 243 described an epoxidation process using alumina as catalyst.

The disadvantage of such prior art processes resides in the fact that, at the end of the reaction, an important work-up procedure is required to eliminate said catalysts which are frequently toxic and pollutant. The final result of such work-up is the formation of important amounts of waste materials which may represent a potential threat for the environment. Furthermore, said work-up may result in the opening, i.e. degradation, of important amounts of the desired lactone or epoxide with the result of a loss of efficiency in the overall process.

There is therefore a need to develop industrial processes for performing Baeyer-Villiger reactions, as well as epoxidations of olefins, which are more environment friendly, e.g. of the so-called "green-chemistry" type.

SUMMARY OF THE INVENTION

The present invention provides a new process for the oxidation of a substrate containing a non-aromatic or non-enonic ethylenic bond or a non-conjugated cyclic ketone into the corresponding epoxide, respectively lactone, using $H_2O_2$ as oxidant, a content in water of the reaction medium below 15% w/w and, as sole catalyst, an alkaline or alkaline earth salt or complex or a mixture of said salts or complexes. The invention also relate to an oxidizing agent consisting of an inert organic solvent, an appropriate amount of $H_2O_2$, a catalytic system and less than 15% w/w of water.

DETAILED DESCRIPTION OF THE PREFERRED EMBODIMENTS

In order to solve the problems aforementioned, the present invention provides a new process involving soft conditions and aimed at the oxidation of a substrate containing:

i) a non-aromatic or non-enonic ethylenic bond; or ii) a non-conjugated cyclic ketone, into the corresponding epoxide or lactone, said process being carried out in an inert solvent using $H_2O_2$ as oxidant and in the presence of a catalytic system, said process being characterized in that the content in water of the reaction medium is below 15% w/w and the catalytic system consists of a compound selected from the group consisting of the alkaline and alkaline earth metal salts or complexes and mixtures of said salts or complexes.

Thus, the invention's process presents the advantage that the addition of the percarboxylic acid derivatives or precursor, or of heavy metal derivatives, to the reaction medium, for example as co-reactant or co-catalyst, is avoided.

By the expression "percarboxylic acid derivative" we mean here any compound comprising a functional group of formula

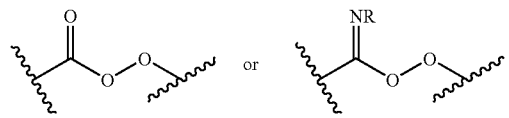

wherein R represents a hydrogen atom or any group containing a carbon or oxygen atom. Furthermore, by the expression "heavy-metal metal derivatives" we mean here any compound containing a metal which is not an alkaline or alkaline-earth metal, that includes, for example, transition metal, aluminum, boron and lanthanide complexes and oxides.

Indeed, we have now surprisingly discovered that, under the appropriate experimental conditions, meaning a content in water of the reaction medium below 15% w/w, an alkaline or alkaline earth derivative is able to promote the oxidation by $H_2O_2$ of a substrate which would otherwise have been inert.

By the expression "non-aromatic or non-enonic ethylenic bond" we mean here an olefin wherein the C=C function is not part of an aromatic system or is not conjugated with a carbon-oxygen double bond.

Similarly, by the expression "non conjugated cyclic ketone" we mean here a C=O functional group, in which the carbon atom is part of a cyclic hydrocarbon moiety, and which is not conjugated with a carbon-carbon double bond or a carbon-heteroatom double bond. It is noteworthy that α,β-unsaturated carbonyl or enone groups do not react if used as substrates in the invention's process, contrary to the chemistry observed first by by E. Weitz, (see for example H.O. House et al., in J. Am. Chem. Soc., 1958, 80, 2428)

From now on, the substrate containing a non-aromatic or non-enonic ethylenic bond or a non-conjugated cyclic ketone, will be referred as "substrate"

According to a first embodiment of the invention, the substrate is selected from the group consisting of a compound of formula (I) and a compound of formula (II)

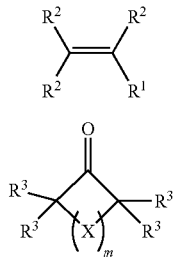

wherein the $R^1$ group represents a linear, branched or cyclic $C_1$ to $C_{20}$ saturated or unsaturated hydrocarbon group, optionally substituted;

the $R^2$ groups represent each a radical selected in the group consisting of a hydrogen atom and a linear, branched or cyclic $C_1$ to $C_{20}$ saturated or unsaturated hydrocarbon group, optionally substituted; two of said $R^2$ groups or a $R^2$ group and the $R^1$ group are optionally bonded together to form a non-aromatic $C_5$ to $C_{20}$ saturated or unsaturated ring in the form of a mono-, bi- or tricyclo derivative, optionally substituted;

the index m represents an integer from 1 to 10;

the $R^3$ groups represent each a radical selected in the group consisting of a hydrogen atom and a linear, branched or cyclic $C_1$ to $C_{20}$ saturated or unsaturated hydrocarbon group, optionally substituted; at least two of said $R^3$ groups are optionally bonded together to form a $C_5$ to $C_{20}$ saturated or unsaturated ring in the form of a mono-, bi- or tricyclo derivative, optionally substituted;

the X groups represent each a $R^3C\!\!=\!\!CR^3$ or a $C(R^3)_2$ group; and said $R^1$, $R^2$, $R^3$ groups and the possible rings formed by said groups may optionally contain up to five functional groups selected from the group consisting of a carbonyl, a carboxyl and an ether.

Possible substituents of said $R^1$, $R^2$ and $R^3$ groups and of the possible rings formed by said groups include $C_1$ to $C_6$ alkyl or alkenyl groups, $OR^4$ groups, carbonyl groups, ester moieties of formula $COOR^5$, acetylenic moieties of formula $C\!\!=\!\!CR^4$, halogen atoms, $C_2$ epoxides and nitro groups, $R^4$ representing a hydrogen atom or a $C_1$ to $C_6$ saturated or unsaturated group, and $R^5$ representing a $C_1$ to $C_6$ saturated or unsaturated group.

By the expression "saturated or unsaturated", hydrocarbon group or ring, we mean here a group which, for example, is an aromatic, alkylaromatic, alkyl, alkenyl, alkadienyl or alkatrienyl derivative.

When a substrate of formula (I) or (II) is employed in a process according to the invention, then the corresponding epoxides or lactones which is produced, is of the formula

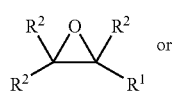

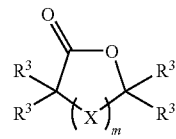

wherein m, X, $R^1$, $R^2$ and $R^3$ have the meaning indicated in the formulae (I) and (II).

According to a particular mode of realization of the first embodiment of the invention, the invention's process is particularly interesting for the oxidation of a substrate of formula (I) or (II) wherein the $R^1$ group represents a linear, branched or cyclic $C^1$ to $C_{10}$ saturated or unsaturated hydrocarbon group, optionally substituted;

the $R^2$ groups represent each a radical selected in the group consisting of a hydrogen atom and a linear, branched or cyclic $C_1$ to $C_{10}$ saturated or unsaturated hydrocarbon group, optionally substituted; two of said $R^2$ groups or a $R^2$ group and the $R^1$ group are optionally bonded together to form a non-aromatic $C_5$ to $C_{14}$ saturated or unsaturated ring in the form of a mono-, bi- or tricyclo derivative, optionally substituted;

the index m represents an integer from 1 to 4;

the $R^3$ groups represent each a radical selected in the group consisting of a hydrogen atom and a linear, branched or cyclic $C_1$ to $C_{10}$ saturated or unsaturated hydrocarbon group, optionally substituted; at least two of said $R^3$ groups are optionally bonded together to form a $C_5$ to $C_{14}$ saturated or unsaturated ring in the form of a mono-, bi- or tricyclo derivative, optionally substituted;

the X groups represent each a $R^3C\!\!=\!\!CR^3$ or a $C(R^3)_2$ group; and said $R^1$, $R^2$, $R^3$ groups and the possible rings formed by said groups may optionally contain up to five functional groups selected from the group consisting of a carbonyl, a carboxyl and an ether.

It is understood that, according to the general definition of the substrate, in the above-mentioned modes of realization the functional groups which may be present in said $R^1$ to $R^3$ groups are not conjugated with the ethylenic bond or the ketone to be oxidized.

According to a second embodiment of the invention, the substrate is a triglycerid oil of formula

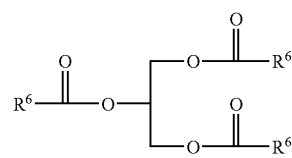

wherein the $R^6$ groups represent each a linear or branched $C_2$ to $C_{20}$ alkenyl, alkadienyl or alkatrienyl group. Preferably, the $R^6$ groups represent each a linear or branched $C_{14}$ to $C_{20}$ alkenyl, alkadienyl or alkatrienyl group.

According to a further mode of realization of the invention's embodiments, useful substrates are those which are susceptible of providing epoxides or lactones which are useful intermediates or end products in the field of perfumery, flavors, food, agrochemical, pharmaceutical or polymer industry. As non limiting examples of the substrates which can be used in said embodiment, one can cite a compound selected from the group consisting of α- and β-pinene, isoamylene, polymers of butadienes, styrenes, unsaturated vegetable or animal oils such as soybean, sunflower, linseed or colza oil, $C_6$ to $C_{18}$ linear or branched monosubstituted olefins, cyclopentanone or cyclohexanone optionally substituted with one or two linear or branched $C_1$ to $C_9$ alkyl or alkenyl groups, $C_{11}$ to $C_{16}$ bi or tricyclo derivatives of octahydronaphthalene such as 9-ethylidene-4-methyl-tricyclo [6.2.1.0(2,7)]undec-4-ene, 4-methyl-tricyclo[6.2.1.0(2,7)] undec-4-ene or 4,7,11,11-tetramethyl-tricyclo 5.4.0.0(1,3)] undec-4-ene and their optical active isomers, and $C_6$ to $C_{16}$ mono-, bi- or tri-cycloalkene derivatives such as cyclooctene, cyclododecene, cyclododecatriene, trimethyl cyclododecatriene, and 4,11,11-trimethyl-8-methylene-tricyclo[7.2.0]undec-4-ene, cedrene and their optical active isomers.

As mentioned above, the invention's process is carried out in the presence of an inert solvent. By the expression "inert solvent" we mean here a solvent which is not oxidized by $H_2O_2$, and does not react with the compounds of formula (I) or (II) under the reaction conditions.

In general, any solvent which is inert under the experimental conditions and is able to solubilize the substrate and $H_2O_2$ is particularly appreciated. In a particular embodiment of the invention, such a solvent is advantageously selected from the group consisting of aromatics, ethers, esters, acyclic ketones, alcohols, glycols, amides, phosphates, halogenated hydrocarbons and the mixture of said solvents. Examples of such solvents are halogenated benzenes or toluenes, $C_4$ to $C_{10}$ ethers, $C_4$ to $C_8$ esters, $C_4$ to $C_7$ acyclic ketones, $C_1$ to $C_6$ primary, secondary or tertiary alcohols, ethylene or propylene glycols as well as the oligomers of ethylene or propylene oxide, $C_4$ to $C_6$ amides, $C_6$ to $C_{24}$ phosphates and methane derivatives containing at least two halogen atoms. As particularly suitable solvents, one can cite chlorobenzene, tert-amyl alcohol, tert-butyl methyl ether, tert-amyl methyl ether, dioxane, ethyl acetate, ethyl propionate, n-propyl acetate, n-propyl formate, butyl formate, isopropyl acetate, butyl acetate and isobutyl acetate.

Furthermore, the inert solvent is advantageously employed in its anhydrous form, e.g. containing less than 5% of water, preferably less than 1%, with respect to the weight of the solvent.

The quantity of solvent used in the invention's process is not really critical, provided that there is enough of it to dilute the reactants or, for example, to allow an efficient elimination or dilution of the water present in the reaction medium. For instance, as non-limiting examples, one may cite quantities ranging between 10% and 80% of the weight of the reaction medium, preferably ranging between 30% and 70%.

Another mandatory element of the invention's process is the catalytic system. By the expression "catalytic system" we mean here the whole set of compounds which are added in the reaction medium to achieve the activation of $H_2O_2$, enabling thus the oxidation of the substrate.

Examples of compounds which may constitute the catalytic system are selected from the group consisting of:

A) the compounds of formula MX, M'X$_2$, R$^7$COOM, (R$^7$COO)$_2$M', M$_2$CO$_3$, MHCO$_3$, M'CO$_3$, MOOH, M$_2$O$_2$, M'O$_2$, MOR$^7$ and M'(OR$^7$)$_2$, M representing an alkaline metal, M' representing an alkaline earth metal, X representing a halogen atom and R$^7$ representing a hydrogen atom or a linear, branched or cyclic $C_1$ to $C_{15}$ alkyl or aromatic group optionally halogenated;

B) the fully deprotonated polycarboxylates of M or M', such as a Na polyacrylates;

C) the alkaline or alkaline earth salts or complexes comprising a ligand selected from the group consisting of $C_5$ to $C_{20}$ β-dialdimine, β-diketimine, β-diketones or β-ketoesters and $C_5$ to $C_{20}$ crown ethers, cryptands, podands or Schiff base; and D) mixtures of the compounds cited in A), B) and C).

The invention's processes wherein the catalytic system is selected from the group consisting of:

E) the compounds of formula R$^8$COOM, (R$^8$COO)$_2$M', M$_2$CO$_3$, MHCO$_3$, M'CO$_3$, M$_2$O$_2$, M'O$_2$, MOR$^8$ and M'(OR$^8$)$_2$, M representing Li, Na or K, M' representing Mg or Ca, and R$^8$ representing a hydrogen atom or a linear, branched or cyclic $C_1$ to $C_8$ alkyl group;

F) the alkaline salts or complexes of formula ML, wherein L is a $C_5$ to $C_{15}$ β-diketonate or deprotonated β-ketoester; and G) mixtures of the compounds cited in E) and F);

have proved to be particularly attractive and convenient.

Examples of R$^8$COO$^-$, $^-$OR$^8$, β-diketonate and deprotonated β-ketoesters are the acetate, propionate, 2-ethyl-hexanoate, naphthenate, benzoate, 2,4-dichlorobenzoate, propylate, ethylate, tert-pentylate, [(CH$_3$)$_3$CCOCHCOC(CH$_3$)$_3$]$^-$, [F$_3$CCOCHCOCF$_3$]$^-$, [C$_6$H$_5$COCHCOCH$_3$]$^-$, [CH$_3$COCHCOCH$_3$]$^-$ and [CH$_3$COCHCOOCH$_2$CH$_2$OCH$_3$]$^-$.

According to a more particular embodiment of the invention, the Li, Na or K salts or complexes cited above give particularly interesting results, especially Li and Na. Similarly, according to a more particular embodiment of the invention, the carbonate, hydrogeno carbonate, acetate, propylate, or $C_5$ to $C_{15}$ β-diketonates salts or complexes cited above are particularly useful.

The quantity of catalyst added to the reaction mixture may oscillate in a relatively large range of values. For instance, as non-limiting examples, one may cite a molar ratio of catalyst per substrate ranging between $10^{-5}$ to 0.9, more preferably between 0.001 and 0.2, or even between 0.005 and 0.1.

The oxidizing agent of the invention is $H_2O_2$. For the purposes of the invention it can be used an aqueous solution of $H_2O_2$, such as 50-70% by weight aqueous solution of hydrogen peroxide. However, as it can be understood from what is described above and below, according to a particular embodiment of the invention it is more advantageous to use a solution of $H_2O_2$ in an organic solvent, as this will contribute to maintain the water contents of the reaction medium as low as possible. Of particular interest are the anhydrous solutions of $H_2O_2$ in an organic solvent, such as a $C_4$-$C_6$ ester or ether, tertio-amyl alcohol or chlorobenzene. By the expression "anhydrous solutions" it is meant here a solution containing less than 5% water, preferably less than 1%. Said solutions can be obtained according to the method described in EP 98427.

Useful quantities of $H_2O_2$, added to the reaction mixture, may be comprised within a relatively large range of values. For instance, as non-limiting examples, one may cite a molar ratio of $H_2O_2$ per function to be oxidized in the substrate of formula (II) ranging between 0.5 to 2, more preferably between 0.9 and 1.2.

Another characteristic of the invention's process is the presence, in the reaction medium, of less than 15% w/w of water. If the amount of water is above said limit, the reaction either does not work at all or produce large amounts of by-products. In fact the lower is the water content of the reaction medium the better it is. Therefore according to a particular embodiment of the invention it is preferred to have a content in water of the reaction medium below 5% w/w, or even less than 1% w/w.

To maintain the water contents into such low limits it is possible, for example, to either use a highly concentrated water solution of hydrogen peroxide and an adequate amount of anhydrous solvent, or use an anhydrous solution of $H_2O_2$ in an organic solvent. Otherwise it is also possible to remove continuously the water, introduced and formed during the process, from the reaction medium. This can be achieved by any means known to a person skilled in the art, for example by an azeotropic distillation.

The temperature at which the process of the invention can be carried out is comprised between 5° C. and the refluxing temperature of the solvent. Preferably, the temperature is in the range of between 60° C. and 140° C. Of course, a person skilled in the art is also able to select the preferred temperature as a function of the melting and boiling point of the starting and final products as well as of the solvent.

According to the simplest mode of realization of the invention, the latter consists of a process for the oxidation of a substrate containing a non-aromatic or non-enonic ethylenic bond or a non-conjugated cyclic ketone into the corresponding epoxide, respectively lactone, by means of an oxidizing agent consisting of an inert organic solvent, an appropriate amount of $H_2O_2$, a catalytic system and less than 15% w/w of water, percentage being relative to the total weight of the oxidizing agent.

Said oxidizing agent is also an object of the present invention. The substrates, as well as the catalytic system, the solvent and $H_2O_2$ are as defined above.

The proportions in which the various ingredients of the oxidizing agent may be admixed together may vary in the following ranges: a) between 2% to 20%, preferably 10% to 15%, for the $H_2O_2$, b) between 0.001% to 10%, preferably 0.1% to 2%, for the catalyst, c) less than 15% of water, and the solvent constitute the balance of the mixture; percentages above being in respect to the total weight of the oxidizing agent.

Preferably, the water content of said oxidizing agent is less than 5% or even 3%.

EXAMPLES

The invention will now be described in further detail by way of the following examples, which are further illustrative of the present invention embodiments, and further demonstrate the advantages of the invention. In said examples the abbreviations have the usual meaning in the art, the temperatures are indicated in degrees centigrade (° C.).

Example 1

Baeyer-Villiger Oxidation of Pentyl Cyclopentanone

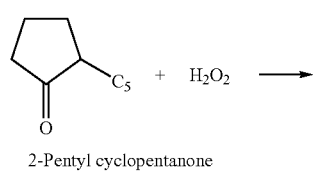

2-Pentyl cyclopentanone

-continued

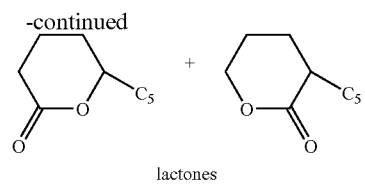

lactones

Procedure A):

In a three-necked 250 ml flask equipped with a magnetic stirrer and a reflux condenser were introduced 31 g of 2-pentyl cyclopentanone (0.2 mole), 31 g of anhydrous ethyl propionate, and 0.048 g (1 mol %) of anhydrous lithium hydroxide. The mixture was brought to reflux at ca. 100° C. Then 57.5 g (0.22 mole) of an anhydrous 13% w/w hydrogen peroxide solution in ethyl propionate, obtained from extraction of a 70% aqueous $H_2O_2$ solution by ethyl propionate, were slowly added over 4 h in the reactor while maintaining the reflux 2 h after the end of the introduction. The reaction mixture was then washed with 10% water to remove the non converted $H_2O_2$, and finally distilled to recover the solvent.

GC analysis of the residue revealed the presence of 18% non converted 2-pentyl cyclopentanone (82% conversion), 73% of lactones and 19% of by-products.

Procedure B):

The reaction was carried out as in Procedure A), but using 0.22 mol of $H_2O_2$ in the form of 70% weight aqueous solution.

The conversion was 53%, with 61% selectivity for the lactones.

Procedure C):

In a three-necked 250 ml flask equipped with a magnetic stirrer and a Dean-Starck reflux condenser were introduced 61.6 g of 2-pentyl cyclopentanone (0.4 mole), 100 g of anhydrous ethyl propionate solvent, and 0.1 g (1 mol %) of anhydrous lithium hydroxide and the mixture was brought to reflux at ca. 110° C. Then 21.5 g (0.44 mole) of 70% w/w aqueous $H_2O_2$ solution were added over 4 h in the reactor and under conditions such as incipient and formed water are removed as a 90:10 ethyl propionate/water azeotropic mixture, ethyl propionate being resent to the reactor. The reaction mixture was then maintained to reflux for two hours, cooled to 30° C., then washed with 10% water to remove the non converted $H_2O_2$, and finally distilled to recover the solvent.

GC analysis of the residue bulb-to-bulb distilled indicated the presence of 0.5% non converted 2-pentyl cyclopentanone (99.5% conversion) and 96% of lactones.

Example 2

Baeyer-Villiger Oxidation of Pentyl Cyclopentanone Using Various Catalysts

This example illustrates the influence of the catalyst used in the Baeyer-Villiger oxidation of 2-pentyl cyclopentanone to lactones by $H_2O_2$.

The reaction was carried out in the presence of 1 mol % catalyst in ethyl propionate as solvent at 110° C. in the same conditions as those reported in Example 1, Procedure C).

The results are reported in Table 1.

TABLE 1

Baeyer-Villiger oxidation using various catalysts

| Experiment | Catalyst | Yield of lactones |
|---|---|---|
| 1 | LiOH | 70% |
| 2 | BaCO$_3$ | 28% |
| 3 | Mg(2-ethyl hexanoate)$_2$ | 52% |
| 4 | CaCO$_3$ | 34% |
| 5 | Na(polyacrylate) | 77% |
| 6 | LiBr | 47% |
| 7 | Na(2-ethyl-hexanoate) | 75% |
| 8 | Na(t-pentoxyde) | 70% |
| 9 | NaHCO$_3$ | 72% |
| 10 | CF$_3$CO$_2$Na | 52% |
| 11 | Li$_2$CO$_3$ | 86% |
| 12 | LiOAc | 83% |
| 13 | KOAc | 36% |
| 14 | Na$_2$O$_2$ | 73% |
| 15 | Li(acac) | 70% |

Yields are calculated in respect of the total amount of substrate used.

When the reaction was carried out in the presence of 1 mol % catalyst in tert-amyl alcohol as solvent at reflux in the same conditions as those reported in Example 1, Procedure C), similar results, reported in Table 1a, were obtained.

TABLE 1a

Baeyer-Villiger oxidation using various catalysts

| Experiment | Catalyst | Yield of lactones |
|---|---|---|
| 1 | LiOH | 88% |
| 2 | NaOH | 92% |
| 3 | NaHCO$_3$ | 84% |

Yields are calculated in respect of the total amount of substrate used.

Example 3

Baeyer-Villiger Oxidation of Pentyl Cyclopentanone Using Various Solvents

This example illustrates the influence of the solvent used in the Baeyer-Villiger oxidation of 2-pentyl cyclopentanone to lactones by 70% w/w aqueous H$_2$O$_2$ solution at 110° C. and in the presence of 1 mol % lithium acetate.

The reaction was carried out under the same conditions as those described in Example 1, Procedure C). The results are reported in Table 2.

TABLE 2

Baeyer-Villiger oxidation using various solvent

| Experiment | Solvent | Yield of lactones |
|---|---|---|
| 1 | Ethyl propionate | 72% |
| 2 | Isopropyl acetate | 51% |
| 3 | Chlorobenzene | 59% |
| 4 | Methyl tert amyl ether | 28% |
| 5 | Dioxane | 30% |

Yields are calculated in respect of the total amount of substrate used.

Example 4

Baeyer-Villiger Oxidation of Various Non-Conjugated Cyclic Ketones

This example illustrates the oxidation of various ketones by 70% w/w aqueous H$_2$O$_2$ solution in ethyl propionate as solvent at 110° C. in the presence of 1 mol % lithium acetate. The reaction was carried out under the same conditions as those disclosed in Example 1, Procedure C). The results are reported in Table 3.

TABLE 3

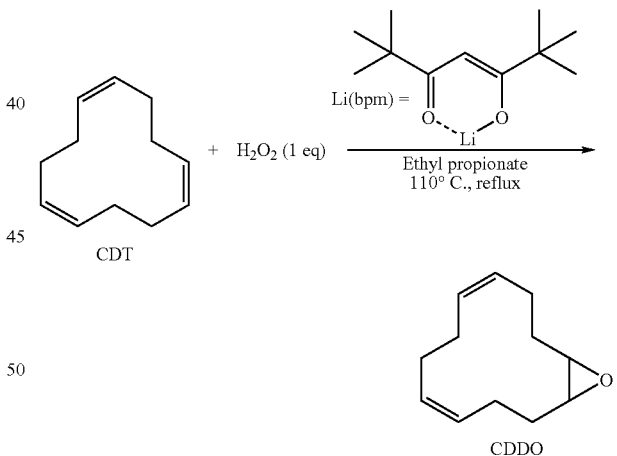

Yields are calculated in respect of the total amount of substrate used.

Example 5

Epoxidation of 1,5,9-cis,trans,trans-cyclododecatriene (CDT)

In a three-necked 250 ml flask equipped with a magnetic stirrer and a Dean-Starck reflux condenser were introduced 64.8 g of CDT (0.4 mole), 100 g of anhydrous ethyl propionate solvent, and 1 mol % of anhydrous lithium bis(pivaloyl) methane [Li(bpm)]. The mixture was brought to reflux at ca. 110° C. and 20 g (0.4 mole) of 70% w/w aqueous H$_2$O$_2$ were added slowly over 4 h in the reactor. The incipient and formed water were removed as a 90:10 ethyl propionate, water azeotropic mixture, ethyl propionate being resent to the reactor. After keeping the reaction mixture under reflux at 110° C., the reactor content was then cooled, and washed with 10% water to remove the non-converted H$_2$O$_2$, and finally distilled to recover the solvent.

Bulb-to-bulb distillation of the residue gave a mixture consisting of 31% CDT, 63% epoxycyclododecadiene (CDDO) and 6% by-products.

Example 6

Epoxidation of CDT Using Various Catalyst

This example illustrates the influence of the catalyst used in the epoxidation of CDT by 70% w/w aqueous $H_2O_2$ in ethyl propionate as solvent at 110° C. The reaction was carried out in the presence of 1 mol % catalyst under the same conditions as those described in Example 5. The results are reported in Table 4.

TABLE 4

Epoxidation using various catalysts

| Experiment | Catalyst | Yield of CDDO |
|---|---|---|
| 1 | $Li_2CO_3$ | 50% |
| 2 | Li(hfacac) | 49% |
| 3 | LiOH | 51% |
| 4 | LiOAc | 43% |
| 5 | Li(benzoylacetone) | 34% |
| 6 | Li(acac) | 23% |
| 7 | Na(bpm) | 25% |
| 8 | Li(dimedone) | 25% |
| 9 | Li(MeOEtAcac) | 20% |

Yields are calculated in respect of the total amount of substrate used.
Bmp = bis(pivaloyl)methane/
hfacac = hexafluoroacetylacetone/
MeOEtAcac = 2-methoxyethyl acetoacetate/
acac = acetylacetonate.

Example 7

Epoxidation of CDT Using Various Solvents

This example illustrates the influence of the solvent used in the epoxidation of CDT by 70% w/w aqueous $H_2O_2$ at 110° C. in the presence of 1 mol % LiOAc under the same conditions as those described in Example 5. The results are reported in Table 5.

TABLE 5

Epoxidation using various solvents

| Experiment | Solvents | Yield of CDDO |
|---|---|---|
| 1 | Tert-amyl alcohol | 39% |
| 2 | Butyl acetate | 38% |
| 3 | Chlorobenzene | 28% |
| 4 | Isopropyl acetate | 23% |
| 5 | Dibutyl ether | 22% |

Yields are calculated in respect of the total amount of substrate used.

Example 8

Epoxidation of Various Substrates

The following examples illustrate the epoxidation of various alkenes by 70% w/w aqueous $H_2O_2$ in ethyl propionate as solvent at 110° C. in the presence of 1 mol % lithium acetate. The reaction was carried out under the same conditions as those described in Example 5. The results are reported in Table 6.

TABLE 6

Epoxidation of various substrates

| Experiment | Substrate | Main product | yield |
|---|---|---|---|
| 1 | | | 56 |
| 2 | | | 66 |
| 3 | | | 75 |

TABLE 6-continued

Epoxidation of various substrates

| Experiment | Substrate | Main product | yield |
|---|---|---|---|
| 4 | 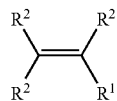 1 : 8 | | 83 |
| 5 | 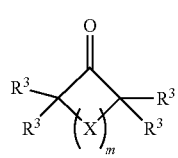 | | 43 |

Yields are calculated in respect of the total amount of substrate used.

What is claimed is:

1. A process for the oxidation of a substrate containing:
   i) a non-aromatic or non-enonic ethylenic bond; or
   ii) a non-conjugated cyclic ketone, into the corresponding epoxide or lactone, said process being carried out in an inert solvent using $H_2O_2$ as oxidant and in the presence of a catalytic system, said process being characterized in that the content in water of the reaction medium is below 15% w/w and the catalytic system consists of a compound selected from the group consisting of the alkaline and alkaline earth metal salts or complexes and mixtures of said salts or complexes;
   wherein the oxidant is not a percarboxylic acid derivative nor does it form a percarboxylic acid or percarboxylic acid derivative during the oxidation.

2. A process according to claim 1, wherein said substrate is selected from the group consisting of a compound of formula (I) and a compound of formula (II)

$$\underset{R^2}{\overset{R^2}{>}}=\underset{R^1}{\overset{R^2}{<}} \quad (I)$$

$$(II)$$

wherein the $R^1$ group represents a linear, branched or cyclic $C_1$ to $C_{20}$ saturated or unsaturated hydrocarbon group, optionally substituted;
the $R^2$ groups represent each a radical selected in the group consisting of a hydrogen atom and a linear, branched or cyclic $C_1$ to $C_{20}$ saturated or unsaturated hydrocarbon group, optionally substituted; two of said $R^2$ groups or a $R^2$ group and the $R^1$ group are optionally bonded together to form a non-aromatic $C_5$ to $C_{20}$ saturated or unsaturated ring in the form of a mono-, bi- or tricyclo derivative, optionally substituted;
the index m represents an integer from 1 to 10;
the $R^3$ groups represent each a radical selected in the group consisting of a hydrogen atom and a linear, branched or cyclic $C_1$ to $C_{20}$ saturated or unsaturated hydrocarbon group, optionally substituted; at least two of said $R^3$ groups are optionally bonded together to form a $C_5$ to $C_{20}$ saturated or unsaturated ring in the form of a mono-, bi- or tricyclo derivative, optionally substituted;
the X groups represent each a $R^3C=CR^3$ or a $C(R^3)_2$ group; and
said $R^1$, $R^2$, $R^3$ groups and the possible rings formed by said groups may optionally contain up to five functional groups selected from the group consisting of a carbonyl, a carboxyl and an ether.

3. A process according to claim 1, wherein the $R^1$ group represents a linear, branched or cyclic $C_1$ to $C_{10}$ saturated or unsaturated hydrocarbon group, optionally substituted;
the $R^2$ groups represent each a radical selected in the group consisting of a hydrogen atom and a linear, branched or cyclic $C_1$ to $C_{10}$ saturated or unsaturated hydrocarbon group, optionally substituted; two of the $R^2$ groups or a $R^2$ group and the $R^1$ group are optionally bonded together to form a non-aromatic $C_5$ to $C_{14}$ saturated or unsaturated ring in the form of a mono-, bi- or tricyclo derivative, optionally substituted;
the index m represents an integer from 1 to 4;
the $R^3$ groups represent each a radical selected in the group consisting of a hydrogen atom and a linear, branched or cyclic $C_1$ to $C_{10}$ saturated or unsaturated hydrocarbon group, optionally substituted; at least two of said $R^3$ groups are optionally bonded together to form a $C_5$ to $C_{14}$ saturated or unsaturated ring in the form of a mono-, bi- or tricycle derivative, optionally substituted;
the X groups represent each a $R^3C=CR^3$ or a $C(R^3)_2$ group; and
the $R^1$, $R^2$, $R^3$ groups and the possible rings formed by said groups may optionally contain up to five functional groups selected from the group consisting of a carbonyl, a carboxyl and an ether.

4. A process according to claim 1, wherein said substrate is a triglycerid oil of formula

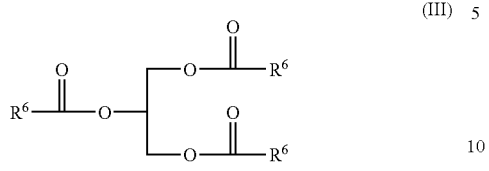
(III)

wherein the $R^6$ groups represent each a linear or branched $C_2$ to $C_{20}$ alkenyl, alkadienyl or alkatrienyl group.

5. A process according to claim 1, wherein the substrate is selected from the group consisting of α and β pinene, isoamylene, polymers of butadienes, styrenes, unsaturated vegetable or animal oils, $C_6$ to $C_{18}$ linear or branched mono-substituted olefins, cyclopentanone or cyclohexanone optionally substituted with one or two linear or branched $C_1$ to $C_9$ alkyl or alkenyl groups, $C_{11}$ to $C_{16}$ bi or tricyclo derivatives of octahydronaphthalene and $C_6$ to $C_{16}$ mono-, bi- or tri-cycloalkene derivatives.

6. A process according to claim 1, wherein the solvent is selected from the group consisting of aromatics, ethers, esters, acyclic ketones, alcohols, glycols, amides, phosphates, halogenated hydrocarbons and mixture of said solvents.

7. A process according to claim 1, wherein the solvent is selected from the group consisting of chlorobenzene, tert-amyl alcohol, tert-butyl methyl ether, tert-amyl methyl ether, dioxane, ethyl acetate, ethyl propionate, n-propyl acetate, n-propyl formate, butyl formate, isopropyl acetate, butyl acetate and isobutyl acetate.

8. A process according to claim 1, wherein the catalytic system consist of a compound selected from the group consisting of:
  A) the compounds of formula MX, M'X$_2$, $R^7$COOM, ($R^7$COO)$_2$M', M$_2$CO$_3$, MHCO$_3$, M'CO$_3$, MOOH, M$_2$O$_2$, M'O$_2$, MOR$^7$ and M'(OR$^7$)$_2$, M representing an alkaline metal, M' representing an alkaline earth metal, X representing a halogen atom and $R^7$ representing a hydrogen atom or a linear, branched or cyclic $C_1$ to $C_{15}$ alkyl or aromatic group optionally halogenated;
  B) the fully deprotonated polycarboxylates of M or M', such as a Na polyacrylates;
  C) the alkaline or alkaline earth salts or complexes comprising a ligand selected from the group consisting of $C_5$ to $C_{20}$ β-dialdimine, β-diketimine, β-diketones or β-ketoesters and $C_5$ to $C_{20}$ crown ethers, cryptands, podands or Schiff base; and
  D) mixtures of the compounds cited in A), B) and C).

9. A process according to claim 1, wherein the catalytic system consists of a compound selected from the group consisting of:
  E) the compounds of formula $R^8$COOM, ($R^8$COO)$_2$M', M$_2$CO$_3$, MHCO$_3$, M'CO$_3$, M$_2$O$_2$, M'O$_2$, MOR$^8$ and M'(OR$^8$)$_2$, M representing Li, Na or K, M' representing Mg or Ca, and $R^8$ representing a hydrogen atom or a linear, branched or cyclic $C_1$ to $C_8$ alkyl group;
  F) the alkaline salts or complexes of formula ML, wherein L is a $C_5$ to $C_{15}$ β-diketonate or deprotonated β-ketoester; and
  G) mixtures of the compounds cited in E) and F).

10. A process according to claim 1, wherein the catalytic system consists of a compound selected from the group consisting of:

E) the compounds of formula $R^8$COOM, ($R^8$COO)$_2$M', MOR$^8$ and M'(OR$^8$)$_2$, M representing Li, Na or K, M' representing Mg or Ca, and $R^8$COO$^-$ are $^-$OR$^8$, are acetate, propionate, 2-ethyl-hexanoate, naphthenate, benzoate, 2,4-dichlorobenzoate, propylate, ethylate, tert-pentylate;
  F) the alkaline salts or complexes of formula ML, wherein L is [(CH$_3$)$_3$CCOCHCOC(CH$_3$)$_3$]$^-$, [F$_3$CCOCHCOCF$_3$]$^-$, [C$_6$H$_5$COCHCOCH$_3$]$^-$, [CH$_3$COCHCOCH$_3$]$^-$ and [CH$_3$COCHCOOCH$_2$CH$_2$OCH$_3$]$^-$; and
  G) mixtures of the compounds cited in E) and F).

11. A process according to claim 1, wherein the catalytic system consists of a compound selected from the group consisting of a carbonate, hydrogeno carbonate, acetate, propylate, or $C_5$ to $C_{15}$ β-diketonates salts or complexes.

12. A process according to claim 1, wherein the content in water of the reaction medium is below 5% w/w.

13. A process according to claim 1, wherein the water is continuously removed from the reaction medium.

14. A process for the oxidation of a substrate containing a non-aromatic or non-enonic ethylenic bond or a non-conjugated cyclic ketone into the corresponding epoxide, respectively lactone, by means of an oxidizing agent consisting of an inert organic solvent, an appropriate amount of H$_2$O$_2$, less than 15% w/w of water, percentage being relative to the total weight of the oxidizing agent, and a catalytic system consisting of a compound selected from the group consisting of the alkaline and alkaline earth metal salts or complexes and mixtures of said salts or complexes, Wherein the oxidant is not a percarboxylic acid derivative nor does it form a percarboxylic acid or percarboxylic acid derivative during the oxidation.

15. An oxidizing agent for use in a process for the oxidation of a substrate according to claim 1, the oxidizing agent consisting of an inert organic solvent, an appropriate amount of H$_2$O$_2$, less than 15% w/w of water, percentage being relative to the total weight of the oxidizing agent, and a catalytic system consisting of a compound selected from the group consisting of the alkaline and alkaline earth metal salts or complexes and mixtures of said salts or complexes Wherein the oxidant is not a percarboxylic acid derivative.

16. A process for the oxidation of a substrate containing:
  i) a non-aromatic or non-enonic ethylenic bond; or
  ii) a non-conjugated cyclic ketone, into the corresponding epoxide or lactone, said process being carried out in an inert solvent using H$_2$O$_2$ as oxidant and in the presence of a catalytic system, said process being characterized in that the content in water of the reaction medium is below 15% w/w and the catalytic system consists of a compound selected from the group consisting of the alkaline and alkaline earth metal salts or complexes and mixtures of said salts or complexes;
wherein:
(A) the substrate is a triglyceride oil of formula

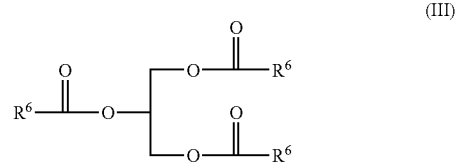
(III)

wherein the $R^6$ groups represent each a linear or branched $C_2$ to $C_{20}$ alkenyl, alkadienyl or alkatrienyl group; or (B) the substrate is selected from the group consisting of α and β pinene, isoamylene, polymers of butadienes, styrenes, unsaturated vegetable or animal oils, $C_6$ to $C_{18}$ linear or branched monosubstituted olefins, cyclopentanone or cyclohexanone optionally substituted with one or two linear or branched $C_1$ to $C_9$ alkyl or alkenyl groups, $C_{11}$ to $C_{16}$ bi or tricyclo derivatives of octahydronaphthalene and $C_6$ to $C_{16}$ mono-, bi- or tri-cycloalkene derivatives;

(C) the solvent is selected from the group consisting of chlorobenzene, tert-amyl alcohol, tert-butyl methyl ether, tert-amyl methyl ether, dioxane, ethyl acetate, ethyl propionate, n-propyl acetate, n-propyl formate, butyl formate, isopropyl acetate, butyl acetate and isobutyl acetate; or (D) the catalytic system consists of a compound selected from the group consisting of:

a) the compounds of formula $R^8COOM$, $(R^8COO)_2M'$, $MOR^8$ and $M'(OR^8)_2$, M representing Li, Na or K, M' representing Mg or Ca, and $R^8COO^-$ are $^-OR^8$, are acetate, propionate, 2-ethyl-hexanoate, naphthenate, benzoate, 2,4-dichlorobenzoate, propylate, ethylate, tert-pentylate;

b) the alkaline salts or complexes of formula ML, wherein L is $[(CH_3)_3CCOCHCOC(CH_3)_3]^-$, $[F_3CCOCHCOCF_3]^-$, $[C_6H_5COCHCOCH_3]^-$, $[CH_3COCHCOCH_3]^-$ and $[CH_3COCHCOOCH_2CH_2OCH_3]^-$; and c) mixtures of the compounds cited in a) and b); or (B) water is continuously removed from the reaction medium.

* * * * *

UNITED STATES PATENT AND TRADEMARK OFFICE
CERTIFICATE OF CORRECTION

PATENT NO. : 7,528,268 B2 Page 1 of 1
APPLICATION NO. : 11/210501
DATED : May 5, 2009
INVENTOR(S) : Mimoun It is certified that error appears in the above-identified patent and that said Letters Patent is hereby corrected as shown below:

Column 14:
Line 29, before "$R^3$", delete "said" and insert -- the --.
Line 60, delete "tricycle" and insert -- tricyclo --.

Column 15:
Line 1, before "substrate", delete "said" and insert -- the --.
Line 2, delete "triglycerid" and insert -- triglyceride --.
Line 27, before "mixture" insert -- a --; and delete "said" and insert -- such --.

Column 16:
Line 23, after "epoxide," insert -- or --.
Line 30, delete "Wherein" and insert -- wherein --.
Line 31, delete "forma" and insert -- form a --.
Line 40, delete "Wherein" and insert -- wherein --.

Column 18:
Line 13, delete "(B)" and insert -- (E) --.

Signed and Sealed this

Ninth Day of June, 2009

JOHN DOLL
*Acting Director of the United States Patent and Trademark Office*